United States Patent [19]

Tenerz et al.

[11] Patent Number: 5,125,058
[45] Date of Patent: Jun. 23, 1992

[54] FIBER OPTIC CONNECTION AND METHOD OF MEASURING INTRAVASCULAR PRESSURE USING SAME

[75] Inventors: Lars Tenerz; Dan Akerfeldt, both of Uppsala, Sweden

[73] Assignee: Radi Medical Systems AB, Uppsala, Sweden

[21] Appl. No.: 727,936

[22] Filed: Jul. 10, 1991

[30] Foreign Application Priority Data

Jul. 11, 1990 [SE] Sweden ............................ 9002415

[51] Int. Cl.$^5$ .......................... G02B 6/38; H01J 5/16; A61B 17/22
[52] U.S. Cl. ........................................ 385/66; 385/12; 385/70; 385/74; 250/227.11; 606/7; 606/15; 606/16; 128/634; 128/637; 128/898
[58] Field of Search ............... 350/96.10, 96.15, 96.18, 350/96.20, 96.21, 96.29, 96.30, 320; 250/227.11, 227.14, 227.28, 231.19; 606/15, 16, 7; 128/634, 637, 898; 385/12, 33, 54, 55, 59, 70, 74, 66, 84, 88, 31

[56] References Cited

U.S. PATENT DOCUMENTS

| | | | |
|---|---|---|---|
| 4,361,380 | 11/1982 | Marazzi | 385/72 |
| 4,606,603 | 8/1986 | Cairns | 385/69 |
| 4,733,935 | 3/1988 | Gandy | 385/69 |
| 4,750,803 | 6/1988 | Schmidt | 385/72 |
| 4,770,486 | 9/1988 | Wang et al. | 385/92 |
| 4,801,187 | 1/1989 | Elbert et al. | 385/31 |
| 4,848,339 | 7/1989 | Rink et al. | 606/7 X |
| 4,986,628 | 1/1991 | Lozhenko et al. | 385/31 |
| 5,007,704 | 4/1991 | McCartney | 385/56 |

FOREIGN PATENT DOCUMENTS

| | | | |
|---|---|---|---|
| 8500104-8 | 11/1985 | Sweden | 385/12 X |
| 8602836-2 | 2/1988 | Sweden | 385/12 X |
| 8603304-0 | 3/1988 | Sweden | 385/12 X |

Primary Examiner—Brian Healy
Attorney, Agent, or Firm—Foley & Lardner

[57] ABSTRACT

The present invention relates to a fiber optic connection (1) between a sensor-guide portion (2) comprising an optic fiber (4) arranged in an air channel, said optic fiber (4) leading to a sensor element in the farther end of said sensor-guide portion (2), and a connective portion (3) comprising an optic fiber (8) arranged in an air channel, said optic fiber (8) leading to an electronic unit, wherein said optic fiber (4) said sensor-guide portion (2) and said optic fiber (8) of said connective portion (3) being aligned against each other in fixed, light transmitting position when said connection (1) is closed, and an outwards pressure tight air channel (11) is formed in the closed position of said connection, said air channel (11) extending continuously from said electronic unit to said sensor element via said connection (1). Furthermore, the invention relates to use of the connection (1) during intravascular pressure measuring, especially of artherosclerotic vessels.

18 Claims, 3 Drawing Sheets

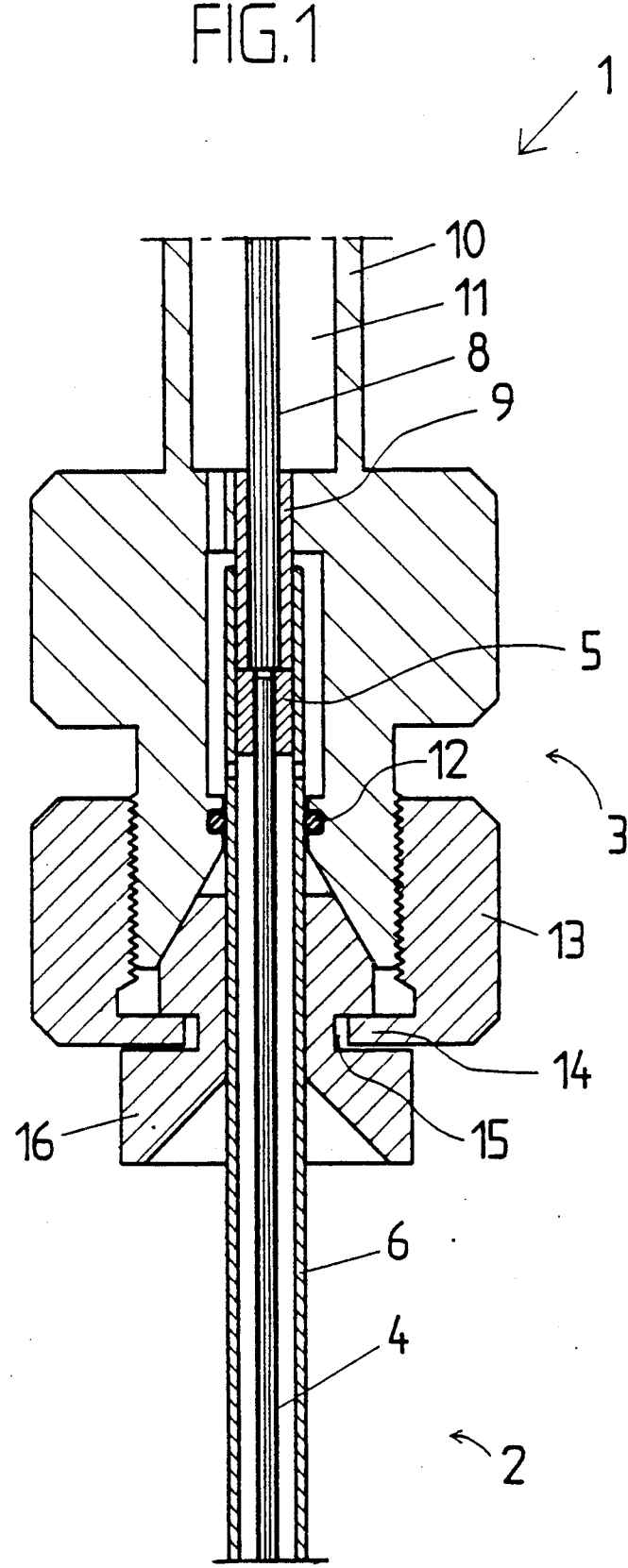

FIBER OPTIC CONNECTION AND METHOD OF MEASURING INTRAVASCULAR PRESSURE USING SAME

BACKGROUND OF THE INVENTION

The present invention relates to a fiber optic connection and use thereof during measurement of intravascular pressure, and more specifically during measurement of pressure in a vessel of an atherosclerotic patient.

In connection with percutaneous transluminal angioplasti (PTA) and percutaneous transluminar coronar angioplasti (PTCA) of atherosclerotic patients it is often desirable to measure the pressure gradient in front of and behind the stenosis in the vessel. In the PTA-method a balloon catheter is used being inflated to dilate the vessel in the area in which the stenosis is situated. Besides enabling the determination of the existence of stenosis, the pressure measurement can also be used to determine the extension of the stenosis and to evaluate if the PTA-method has been successful.

A pressure sensor being mounted to a guide and connected to an electronic unit is described in the patent applications Nos. SE 85 001048, SE 86 02836-2 and SE 86 03304-0, to which are referred. The known pressure sensor comprises a guide-sensor portion, being intended for insertion into the body, and a connective portion, connecting the air channel disposed along the sensor-guide portion and the optic fiber to the electronic unit. The properties of the guide portion, i.e. its ability to search its way in the vessels, is determined by its flexibility, torsion resistance, radiopacity etc, while the connective portion is formed for easy handling outside the body. When measuring pressure the pressure sensor can easily be inserted to desired position in a catheter already inserted in a blood vessel. The size, i.e. the diameter, of the sensor guide portion is limited by the inner diameter of the catheter while the connective portion leading to the electronic unit can have the coarseness required for stability and easily handling since it is independent of dimension.

A drawback with the known pressure sensor, being mounted on a guide and connected to an electronic unit, is that it is not possible to change catheter, e.g. from a balloon catheter to a diagnostic catheter with the pressure sensor in its place in the vessel since the sensor guide portion is rigidly coupled to the connective portion of the electronic unit which means that the whole construction must be withdrawn if a catheter exchange is needed. The reason why it is desireable to have the pressure sensor placed in the vessel is that the stenosis should be passed as few times as possible for the safety of the patient. Another drawback is that it is not possible to first put the guide-sensor in place in the vessel and thereafter thread a catheter over it. With the known construction one has to first bring out the sensor-guide portion during catheter exchange, thereafter insert a conventional guide into the catheter, pull out the catheter with a conventional guide left in the vessel, thereafter proceed in the same way as for the insertion of the first catheter, i.e. thread over the new catheter, pull out the conventional guide and eventually insert the sensor-guide portion.

A possible solution on the problem would be a releaseable connection between the sensor-guide portion and the connective portion. Such a connection would have to establish pneumatic and optic connection between the two portions.

SUMMARY OF THE INVENTION

The present invention solves the above problem by providing a fiber optic connection according to the characterizing features of claim 1.

BRIEF DESCRIPTION OF THE DRAWINGS

The invention will now be described closer in relation to the accompanying drawings, in which FIG. 1 is a longitudinal section through the connection according to the present invention in its closed position;

DETAILED DESCRIPTION OF THE PREFERRED EMBODIMENTS

Figure 2A:
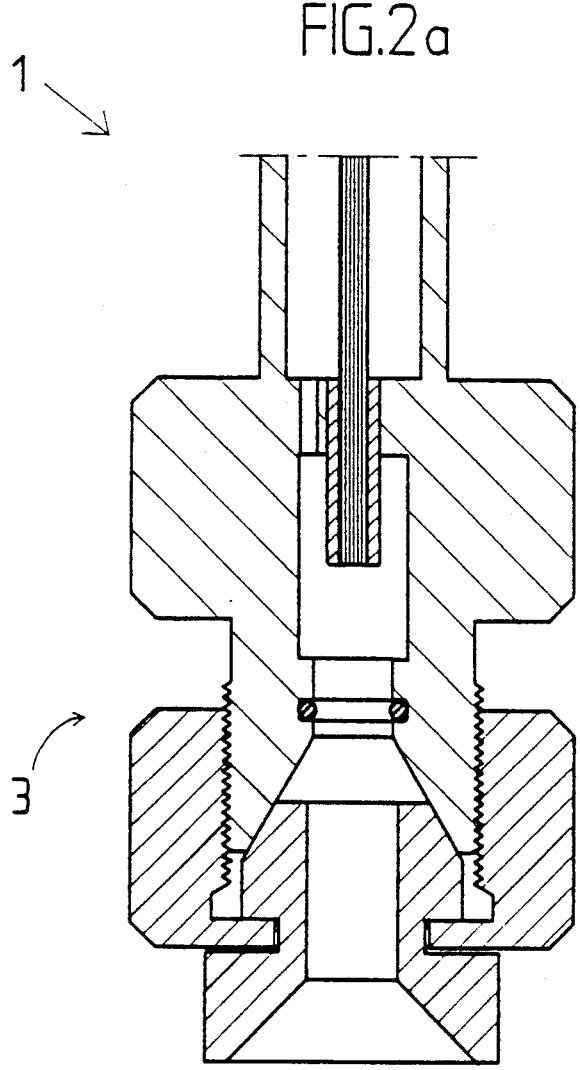
FIGS. 2a–2b is a longitudinal section according to FIG. 1 but showing the connection in its separated position.

In FIG. 1 a closed fiber optic connection 1 is shown according to the present invention. The connection 1 comprises mainly two parts, namely a thin sensor-guide portion 2 comprising a signal transmitting optic fiber 4, on the distal or farther end of which being intended for insertion to the pressure measuring site in the stenosis vessel, a not shown sensor element, e.g. a pressure gauge, is situated, and a connective portion 3 leading to a not shown electronic unit. The fiber 4 of the sensor-guide portion 2 is centrated in a short glass or metal tube 5, being fixed in a flexible cannula tube or processed tube 6. The tube 6 can be surrounded by a tube 7 extending along the whole of tube 6 except for the upper end of the tube 6 where two air holes 6' are situated, the importance of which will be described more closely below. The tube 7 can be made of e.g. Teflon ® being biocompatible and sliding easily against the vessel walls. The fiber 4 is fastened with an axial distance of about 35–50 μm from the front portion of the tube 5, giving a distinct distance between the fiber 4 and the fiber 8 of the connective portion 3. This is important to obtain a robust connection independent of interference phenomena. The coarseness of the tube 7 is limited since the connective portion 3 has to fit in the catheter.

The other portion of the connection, i.e. the connective portion 3, comprises a signal transmitting optic fiber 8 connected to a not shown electronic unit. The optic fiber 8 in the shown embodiment is coarser than the fiber 4, which permits greater coaxiality tolerances when centrating the fibers 4 and 8 against each other. Another reason for having a coarser fiber 8 is that increased stability and easy handling is achieved but it is appreciated that the fiber 8 can be as coarse as the fiber 4. Furthermore, the fiber 8 is centrated and fixed in a forward glass or metal tube 9, the lower portion of which is enclosed in the tube 6 when the connection is closed. The fibers 4 and 8 do not need to be exactly perpendicularly cut because of the above describe distance of 35–50 μm between the fibers. In this way the fibers 4 and 8 are situated coaxially against each other for optimal light transmission. It is also possible to arrange a lense/lenses in the end/ends of the fiber 4 and-/or 8 facing towards each other. The fiber 8 in the connective portion 3 is dimension independent unlike the fiber 4 in the sensor-guide portion 2, which fiber 4 shall have as small diameter as possible to fit in small catheters. The tube 9 is centrated in a male sleeve 10 having an air channel 11 being pressure tight against the environment. The air channel 11 extends continuosly from the electronic unit to the sensor element. From the upper space between the fiber 8 and male sleeve 10 the air channel 11, via a channel on the outside of the tube 9, extends downwards and into the tube 6 via the air holes 6' and continues to the sensor element in the space between the fiber 4 and the tube 6. The purpose of the air channel 11 is to pneumatically connect the sensor element with the electronic unit in such a way that the same pressure is obtained on both sides of the connection 1. The pneumatic connection between the sensor function and the electronic unit enables application of a reference pressure in the air channel 11 for calibration purposes and maintaining of the set position and stable signals after separation of the connection and following joining thereof. At the actual pressure measuring, atmospheric pressure is used in the air channel 11. The lower portion of the male sleeve 10 has a sealing function against the tube 6 below the air holes 6', which sealing also functions as a tensile release. Alternatively the sealing can be achieved by a rubber ring 12, threading, bayonet joint etc, lying sealingly against the tube 6 when the connection is closed. The lower portion of the male sleeve 10 is threaded on the outside and cone-shaped on the inside. The threading of the male sleeve 10 is adapted to an inner threading on an female sleeve 13, the sleeves 10 and 13 forming a fitting. The female sleeve 13 is in this embodiment in the lower portion provided with an inwards directed flange 14, travelling in a groove 15 of an inner sleeve 16. This allows lateral movement so that the pressure against the tube 6 becomes evenly distributed. The upper portion of the sleeve 16 is cone-shaped on the outside. In the closed position of the connection the outer cone shape of the sleeve 16 presses against the inner cone shape of the female sleeve 13, whereby the tube 7 is fixed in a rigid position by the female sleeve 13. It is appreciated that the female sleeve 13 and the sleeve 16 can be formed in one piece, the flange 14 and groove 15 being omitted.

Figure 2B:
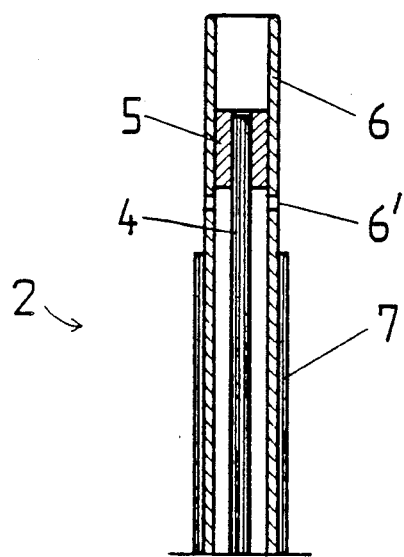

In FIG. 2a-2b the separated position of the connection is shown. To separate the connection the female sleeve 13 is screwed downwards a distance, whereby the grip of the sleeve 16 above the tube 6 is released so that the sensor-guide portion 2 and the connective portion 3 easily can be separated from each other. Thus the connection 1 is achieved by mechanically joining the portions 2 and 3, whereby an optic connection is obtained comprising an air channel being pressure tight against the outside. In the shown embodiments the tube 6 has an female function while the tube 9 has an male function, but it is of course possible to use an opposite solution.

In the embodiment according to FIGS. 1-2a, 2b the fibers 4 and 8 are centrated in the connection 1. An alternative embodiment would be to centrate the fibers with one of or both of the fibers lying excentrically and rotation safely against the inner surface of the respective fixation tube and axially with a distance according to the above mentioned. The air channel 11 would then only be situated on one side of the fiber/fibers and not about the fibers as in the shown embodiment.

To optimize the light transmission and allow greater centration tolerances between the fibers 4 and 8 a lense can be arranged in the fiber 4 and/or the fiber 8 at the connection 1. If a lense is only arranged in the fiber 4 the fiber 8 is suitably coarser than the fiber 4.

Figure 3:
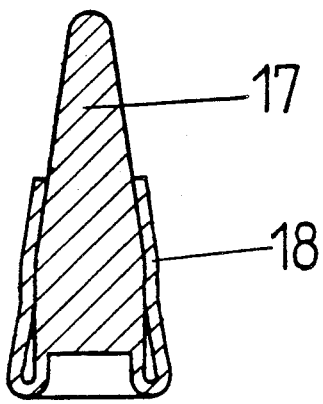
FIG. 3 shows a protective cap for the front portion of the sensor-guide portion to be used during catheter exchange.
Figure 5:
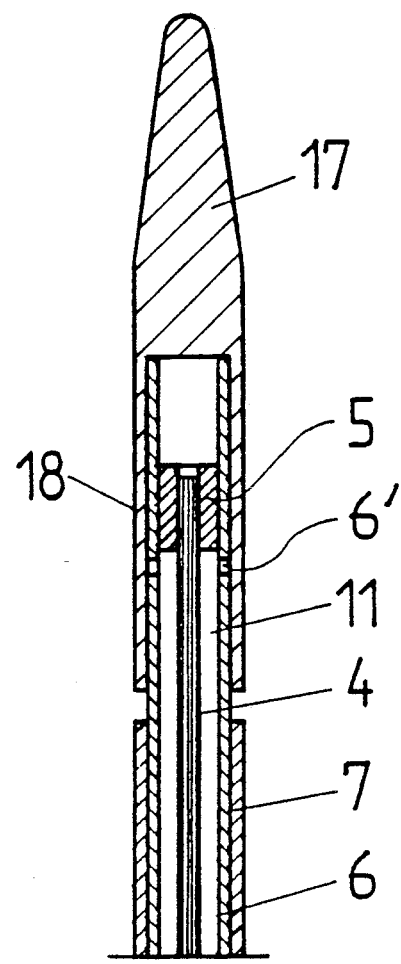
FIG. 5 shows the protective cap according to FIG. 3 or 4 arranged on the front portion of the sensor-guide portion.
Figure 4:
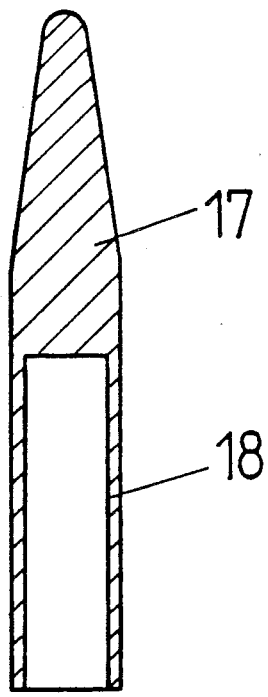
FIG. 4 shows an alternative protective cap.

In the FIGS. 3-5 a detail of the present invention is shown. During catheter exchange it is necessary to prevent that liquid contacts the fiber 4 or gets into the air channel 11 to avoid occlusion. A way to prevent this is to arrange a protective cap 17 over the front portion of the sensor-guide portion 2 during the catheter exchange so that air holes 6' and forward end of the tube 6 stay protected during the exchange. The protective cap 17 is provided with walls 18, which can be rollable (FIG. 3) or pullable (FIG. 4) over the front portion of the tube 6. The protective cap 17 should be of a lesser dimension to secure a tight contact against the tube 6. The protective cap 17 is arranged by hand or by a not shown auxilary fixture. An alternative way to protective the sensor-guide portion 3 during catheter exchange is to arrange a protective tube of rubber material over the air holes 6'.

Below the use of the connection according to the present invention will be described.

At first a sensor-guide portion 2 and connective portion 3 are mounted via the connection 1 and thereafter a calibration of the sensor element is performed in vitro, whereby several different reference pressures are applied in the air channel 11 to establish a calibration curve. Thereafter, the connection 1 is separated and a protective cap is arranged on the sensor-guide portion as described above. During balloon dilating of stenotic vessels, for example, the sensor-guide portion 2 provided with the protective cap 17 is first inserted in the vessel, often a coronar vessel, via the femoral artery. Thereafter, the treatment catheter is threaded over the sensor-guide portion 2 and forwarded to the vessel. Next step is to remove the protective cap 17 and connect the connective portion 3 to the sensor-guide portion 2, whereafter pressure measurement is performed in the stenotic vessel. If it in the next step is desireable to change treatment catheter, the connection is broken, whereafter the protective cap 17 is mounted, the catheter is withdrawn, the new catheter is threaded on the sensor-guide portion 2, the protective cap 17 is removed, the connection between the portions 2 and 3 is re-established and renewed blood pressure measuring is performed. Thus it appears that several steps, in which the senosis has to be passed, can be avoided according to the present invention.

According to the present invention there is no need for recalibration after joining. It is however possible that the calibration can be altered if liquid gets into the connection and for safety reasons the calibration is performed again after the joining. If the reference values have changed compared to the first calibration, the measure range is displaced correspondingly.

Optional recalibration of the sensor element, to compensate for possible light losses at the joining, can be performed in vivo as follows:

At first, such an high pressure is applied in the air channel 11 that the signal from the sensor element reaches its absolute maximum, whereby the intensity of the signal is registrated at this maximum. Thereafter an overpressure is applied in the air channel 11 so that the sensor element reaches its absolute minimum, whereby the intensity of the signal is registrated at this minimum. Since the sensor is in the bottom position at minimum and maximum readings the blood pressure does not effect the signal. The measure range is between the mimimal and maximal value. These values are compared with the max and min values being obtained at the in vitro calibration enabling possible corrections to be made.

What is claimed is:

1. Fiber optic connection (1) between a sensor-guide portion (2) comprising a first optic fiber (4) disposed in a first air channel, said first optic fiber (4) leading to a sensor element in a farther end of said sensor-guide portion (2), and a connective portion (3) comprising a second optic fiber (8) disposed in a second air channel, said second optic fiber (8) leading to an electronic unit, wherein said first optic fiber (4) of said sensor-guide portion (2) and said second optic fiber (8) of said connective portion (3) being aligned against each other in fixed, light transmitting position when said connection (1) is in a closed portion, and an outwards pressure tight air channel (11) formed in the closed position of said connection, said pressure tight air channel (11) extending continuously from said electronic unit to said sensor element via said connection (1).

2. A connection according to claim 1, wherein a front portion of said first fiber (4) is centrated in a short tube (5) being fixed in a second tube (6), said second tube (6) extending a short distance in front of said short tube (5) to the sensor element at the farthest end of said sensor guide, said second fiber (8) being centrated and fixed inside an additional tube (9) being disposed in the front portion of said second tube (6) in the closed position of said connection (1) whereby said additional and short tubes (9) and (5) are fitted against each other in the closed position of said connection and said first and second fibers (4) and (8) are coaxially aligned against each other.

3. A connection according to claim 1, wherein at least one of said first fiber (4) and said second fiber (8) is eccentrically disposed in said connection (1).

4. A connection according to claim 1, wherein said second fiber (8) is coarser than said first fiber (4).

5. A connection according to claim 1, wherein said first and second fibers (4, 8) are disposed with a distance therebetween of about 35–50 μm.

6. A connection according to claim 2, further comprising a male sleeve (10) in which said additional tube (9) is centrated and in which said pressure tight air channel (11) begins, said pressure tight air channel (11) extending around said second fiber (8), via a channel on the outside of said additional tube (9), said second tube (6) further comprising a plurality of holes, said pressure tight air channel extending into said plurality of holes (6') and into said sensor-guide portion and to said sensor element, and said male sleeve (10) having a sealing connection to said second tube (6) beyond said holes (6').

7. A connection according to claim 6, wherein the sealing connection between said male sleeve (10) and said second tube (6) is a rubber ring (12).

8. A connection according to claim 6, further comprising a female sleeve (13) with a conical surface on the outside and a threading on the inside, wherein said male sleeve (10) comprises a lower portion with a conical surface on the inside and threading on the outside being engaged with the threading on the inside of said female sleeve (13), said female sleeve (13) having a conical shape on the outside, whereby the conical surface of said female sleeve (13) is pressed upwards against the conical surface of said male sleeve (10) when said female sleeve (13) is threaded upwards in such a way that said tube (6) is fixed in the closed position of said connection.

9. A connection according to claim 8, wherein said female sleeve (13) further comprises an inner sleeve (16) with a groove (15) functioning as a sealing between said male sleeve (10) and said second tube (6), and wherein said female sleeve (13) is provided with a lower inwards directed flange (14) travelling in the groove (15) of said inner sleeve (16).

10. A connection according to claim 2, further comprising a third tube (7) of biocompatible easily gliding material arranged over said second tube (6), said second tube further comprising a plurality of air holes, said third tube (7) extending from said sensor element to but not sealing said air holes (6').

11. A connection according to claim 1, further comprising a lens placed in at least one of the farther end of said connective portion (3) and a front end of said sensor-guide portion (2), to optimize light transmission and allow greater centration tolerances of said first and second fibers (4, 8) against each other.

12. A connection according to claim 1, further comprising a lens placed on said first fiber (4), and wherein said second fiber (8) is coarser than said first fiber (4).

13. A method of measuring intravascular pressure comprising the steps of:
(a) positioning a first optic fiber (4) in a first air channel, the first optic fiber leading to a sensor element in a farther end of a sensor-guide portion (2);
(b) positioning a second optic fiber (8) in a second air channel in a connective portion (3), the second optic fiber (8) leading to an electronic unit;
(c) connecting said first optic fiber and second optic fiber in a fiber optic connection (1) between said sensor-guide portion (2) and said connective portion (3);
(d) closing said first optic fiber (4) and said second optic fiber (8) of said sensor-guide portion (2) in a fixed, light transmitting position;
(e) forming an outwards pressure tight air channel (11) extending continuously from said electronic unit to said sensor element via said connection;
(f) inserting the sensor-guide portion into a vessel; and
(g) measuring intravascular pressure through said connection.

14. A method according to claim 13 further comprising at least one of the steps of opening and further closing the connection during at least one of a procedure of percutaneous transluminal angioplasti (PTA) and percutaneous transluminar coronar angioplasti (PCTA).

15. A method according to claim 13, further comprising at least one of the steps of threading a catheter over said sensor-guide portion (2) of said connection whereby it is used as a conventional guide and measuring pressure with the sensor-guide portion.

16. A method of measuring intravascular pressure, comprising the steps of:
(a) connecting a sensor-guide portion (2), comprising a first optic fiber (4) leading to a sensory element in a farther end of said sensor-guide portion (2), positioned in a first air channel, and a connective portion (3), comprising a second optic fiber (8) leading to an electronic unit, positioned in a second air channel;

(b) enclosing said first optic fiber (4) and said second optic fiber (8) of said sensor-guide portion (2) in a fixed, light transmitting position;
(c) forming an outwards pressure tight air channel (11) around said first and second fibers, extending continuously from said electronic unit to said sensor element;
(d) inserting said sensor-guide portion (2) in a vessel after forming said pressure tight air channel (11) between said sensor-guide portion (2) and said connective portion (3); and
(e) calibrating said sensor element in vitro by applicating a plurality of different reference pressures in said pressure tight air channel.

17. A method according to claim 16 wherein, the connecting and forming steps are performed after the inserting step, and the calibrating step further comprises the steps of applying a high negative pressure so that said sensor element reaches its absolute maximum, and thereafter applying a high positive pressure so that said sensor element reaches its absolute minimum, and registering and comparing a plurality of signal intensities at the maximum and minimum with a plurality of maximal and minimal values from an in vitro calibration.

18. A method according to claim 16, further comprising the steps of placing a front portion of said sensor-guide portion (2) in a tube (6) having a plurality of air holes (6'), placing a protective cap (17) over the front portion of said sensor-guide portion (2) and over said air holes (6') in said tube (6) to protect said sensor-guide portion (2) during insertion in a vessel and during threading of a catheter, and removing said protective cap (17) before at least one of the steps of connecting, enclosing, and forming.

* * * * *